United States Patent
Daitou et al.

(10) Patent No.: US 6,491,795 B2
(45) Date of Patent: Dec. 10, 2002

(54) PROCESS FOR RECOVERING BENZYL BENZOATE

(75) Inventors: Noboru Daitou, Kitakyushu (JP); Shingo Ueda, Kitakyushu (JP); Ryouji Akamine, Kitakyushu (JP); Kazuyoshi Horibe, Kitakyushu (JP); Katsuhiko Sakura, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/778,838

(22) Filed: Feb. 8, 2001

(65) Prior Publication Data

US 2001/0020579 A1 Sep. 13, 2001

(30) Foreign Application Priority Data

Feb. 17, 2000 (JP) ........................................ 2000-039210

(51) Int. Cl.[7] .............................. B01D 3/00; B01D 9/02; C07C 69/78; C07C 51/44
(52) U.S. Cl. ........................... 203/48; 203/91; 203/100; 203/DIG. 16; 203/38; 23/295; 23/300; 560/106; 562/494; 568/810
(58) Field of Search ............................. 203/48, 291, 63, 203/29, 38, 100, DIG. 16; 568/863, 810; 562/494; 560/106; 23/295, 299, 300, 306

(56) References Cited

U.S. PATENT DOCUMENTS 4,227,017 A * 10/1980 Jongsma ..................... 562/494
5,037,512 A * 8/1991 Schulte-Huermann ....... 203/38

FOREIGN PATENT DOCUMENTS

| JP | 53031639 | 3/1978 |
| JP | 53095934 | 8/1978 |
| JP | 56039045 | 4/1981 |

OTHER PUBLICATIONS

Walter H. C. Rueggeberg et al.; "Industrial and Engineering Chemistry", vol. 38, No. 2, pp. 207–211.

* cited by examiner

*Primary Examiner*—Virginia Manoharan
(74) *Attorney, Agent, or Firm*—Birch, Stewart, Kolasch & Birch, LLP

(57) ABSTRACT

High-purity benzyl benzoate is recovered by distilling the residue remaining after removal of unreacted toluene and benzoic acid from a reaction mixture produced by the oxidation of toluene by molecular oxygen in the presence of a metal catalyst thereby separating a fraction of benzyl benzoate containing 80 wt % or more benzyl benzoate, 10 wt % or less benzoic acid and 10 wt % or less fluorenone, and purifying the fraction of benzyl benzoate by crystallization such as recrystallization. According to this process, it is possible to recover high-purity benzyl benzoate by a simple operation at low cost from the by-product formed in the manufacture of benzoic acid.

16 Claims, No Drawings

PROCESS FOR RECOVERING BENZYL BENZOATE

FIELD OF THE INVENTION

This invention relates to a process for recovering high-purity benzyl benzoate from a reaction mixture obtained by the oxidation of toluene by molecular oxygen.

DESCRIPTION OF THE RELATED ART

Benzyl benzoate is an important compound useful as raw material for perfumes and pharmaceuticals and applicable to other industries and a large number of processes for its manufacture have been reported. For example, Japan Kokai Tokkyo Koho Sho 56-39045 (1981) reports the recovery of benzyl benzoate by distillation of benzyl benzoate under reduced pressure from a reaction mixture produced by the oxidation of toluene by molecular oxygen. However, distillation alone has not yielded benzyl benzoate with such high purity as to be acceptable for use in perfumes. Likewise, Japan Kokai Tokkyo Koho Sho 53-95934 (1978) reports the recovery of benzyl benzoate by distillation from a reaction mixture produced by the oxidation of toluene by molecular oxygen, but high-purity benzyl benzoate is not obtained on account of the difficulty of separating fluorenone whose boiling point is close to that of BZB.

Japan Kokai Tokkyo Koho Sho 53-31639 (1978) describes a process for synthesizing benzyl benzoate by the transesterification of methyl benzoate with benzyl alcohol and an article in Industrial and Engineering Chemistry, Vol. 39, No. 10, pp.1300–1302 (1947) describes the synthesis of benzyl benzoate by the reaction of sodium benzoate with benzyl alcohol. Although these processes yield high-purity benzyl benzoate, they face a problem of high manufacturing cost because of the use of expensive catalysts and raw materials.

SUMMARY OF THE INVENTION

An object of this invention is to provide a process, free from the aforementioned shortcomings, for recovering benzyl benzoate in high purity at low cost.

This invention relates to a process for recovering benzyl benzoate which comprises distilling the residue remaining after removal of unreacted toluene and benzoic acid from a reaction mixture produced by the oxidation of toluene by molecular oxygen in the presence of a metal catalyst thereby separating a fraction of benzyl benzoate containing 80% by weight or more benzyl benzoate and simultaneously 10% by weight or less benzoic acid and 10% by weight or less fluorenone, purifying the fraction of benzyl benzoate by crystallization and recovering high-purity benzyl benzoate.

DETAILED DESCRIPTION OF THE INVENTION

Benzyl benzoate (BZB) is known to be present as by-product in a reaction mixture produced by the oxidation of toluene by molecular oxygen in the presence of a catalyst. In general, the oxidation of toluene is carried out for the purpose of manufacturing benzoic acid and those catalysts which are commonly used for the reaction are based on heavy metals such as cobalt and manganese. As for the normal operating conditions inside the reactor, the temperature is 120–170° C., the pressure is normal to 1 MPa and air is frequently used as molecular oxygen. A reaction mixture produced under any conditions, not limited to the aforementioned conditions or the purpose, may be used in this invention as long as it contains BZB and benzoic acid.

Either a continuous process or a batch process may be chosen for the oxidation reaction, though a continuous process is more economical. The main product to be produced by the oxidation of toluene is benzoic acid, but the following by-products besides unreacted toluene have been identified in the reaction mixture: water, formic acid, acetic acid, propionic acid, acetone, benzene, biphenyl, methylbiphenyl, dimethylbiphenyl, fluorene, fluorenone, toluic acid, phthalic acid, isophthalic acid, terephthalic acid, biphenylcarboxylic acid, methylbiphenylcarboxylic acid, biphenyldicarboxylic acid, and phenylbenzyl alcohol, compounds occurring as intermediates in the oxidation of toluene to benzoic acid such as benzaldehyde and benzyl alcohol, and esters formed by the esterification of benzyl alcohol or phenylbenzyl alcohol with a variety of carboxylic acids inside the reactor such as benzyl benzoate (BZB), benzyl acetate (BZA), benzyl toluate and benzyl biphenylcarb oxylate.

The reaction mixture is successively distilled to recover unreacted toluene and the main product benzoic acid. Simultaneously distilled in this step are components boiling lower than toluene such as water, formic acid, acetic acid, propionic acid, acetone and benzene and an intermediate fraction with a boiling point between those of toluene and benzoic acid such as benzaldehyde and benzyl alcohol. The unreacted raw material toluene and the intermediates benzaldehyde and benzyl alcohol are returned to the reactor for conversion to benzoic acid. Components boiling higher than benzoic acid, for example, biphenyl, methylbiphenyl, dimethylbiphenyl, fluorene, fluorenone, toluic acid, phthalic acid, isophthalic acid, terephthalic acid, biphenylcarboxylic acid, methylbiphenylcarboxylic acid, biphenyldicarboxylic acid, benzyl benzoate (BZB), benzyl acetate (BZA), and benzyl toluate are contained in the residue after the distillation of benzoic acid. Although the composition of the high-boiling components contained in the residue varies with the conditions for reaction and distillation, any residue containing at least a given amount, preferably 5% by weight or more, of BZB is acceptable for use in this invention. The residue may contain heavy metals such as cobalt or manganese originating from the oxidation catalyst, but it is advantageous to extract such heavy metals by hot water.

The BZB contained in the residue is distilled again and recovered as a BZB fraction. Either a continuous process or a batch process may be chosen for the distillation, though a continuous process is preferable economically. The BZB fraction obtained here is purified in the recrystallization step. Economical recovery of high-purity BZB, however, makes it necessary to maximize the recovery and the concentration of the BZB fraction in the distillation step.

The distillation in question is carried out below 270° C., preferably below 250° C., in order to prevent benzoate esters from thermally decomposing to benzoic acid as much as possible when the temperature at the bottom of the distillation column becomes too high and also to prevent benzoic acid from corroding the apparatus. As the boiling point of BZB is 323° C., it is desirable to carry out the distillation under reduced pressure while keeping the pressure at the top of the distillation column preferably at 4.0 Kpa or less.

The number of plates for a distillation column used for the recovery of BZB from the residue will be 5 or more for satisfactory operation and the concentration of the BZB fraction can be controlled by reflux ratio. Providing the distillation column with an unnecessarily larger number of plates will raise the temperature at the bottom of the column on account of the pressure difference inside the column and occasionally cause such problems as formation of by-product benzoic acid and corrosion of the apparatus. The concentration of BZB in the BZB fraction to be obtained by this distillation is preferably 80% by weight or more, more preferably 90% by weight or more, in consideration of the recovery and purity in the following crystallization step. For this reason, the BZB fraction is obtained by carrying out the distillation preferably at 180–220° C., more preferably at 190–210° C., in case the pressure at the top of the distillation column is kept at 2.6 KPa.

The BZB fraction contains, in addition to BZB, such compounds as benzoic acid and fluorenone whose boiling point is close to that of BZB. In case the concentration of BZB in the BZB fraction is less than 80% by weight, the recovery of BZB in the following recrystallization step falls and, at the same time, benzoic acid and fluorenone crystallize together with BZB to lower the purity of the recovered BZB. The presence of less than 10% by weight of benzoic acid in the BZB fraction allows economical recovery of BZB while the presence of benzoic acid in excess of 10% by weight decreases the recovery of BZB in the crystallization step thereby making economical recovery of BZB difficult. In the presence of less than 10% by weight of fluorenone in the BZB fraction, BZB purified in the recrystallization step is colorless and transparent. On the other hand, when fluorenone is present in excess of 10% by weight in the BZB fraction, it crystallizes simultaneously with BZB and, as a result, BZB becomes colored yellow and unsuitable as raw material for perfumes and pharmaceuticals.

The BZB fraction is purified by crystallization to a purity acceptable as raw material for perfumes and pharmaceuticals. Known processes such as recrystallization, recrystallization and solvent washing, dispersive crystallization in solvent, multi-stage crystallization and continuous crystallization can be adopted for purification by crystallization. Advantageous among them is continuous crystallization and recrystallization, crystallization and solvent washing or dispersive crystallization in solvent. Recrystallization is carried out advantageously by dissolving BZB in a solvent that dissolves BZB moderately and is readily separable from BZB and then recrystallizing the BZB. In case the BZB fraction is obtained as liquid, the fraction is dissolved as it is in a solvent and allowed to recrystallize. Any solvent is suitable for this recrystallization if it shows a good solvent power against the BZB fraction above 10° C. but such an insufficient solvent power against BZB below 10° C. as to allow only BZB to crystallize and boils lower than BZB. Such solvents include acetone, methyl isobutyl ketone, methyl ethyl ketone, methanol, ethanol, isopropanol, butanol, tetrahydrofuran, dioxane, benzene, toluene, xylene, ethylbenzene, cyclohexane, methylcyclohexane, ethylcyclohexane, dimethyl ether, diethyl ether and petroleum ether. Two or more of such solvents may be mixed properly or an adequate amount of water may be added to these solvents. An aliphatic alcohol with 1 to 5 carbon atoms such as methanol, ethanol, propanol, butanol and pentanol or its mixture with water is a highly efficient solvent for the purification of BZB. In the case of a mixture of an alcohol and water, the alcohol to water ratio is preferably in the range from approximately 1:2 to 2:1.

Crystallization and solvent washing is effected by washing with a solvent the crystals formed by cooling the BZB fraction. A preferable procedure for washing is dispersing the crystals in a solvent followed by solid-liquid separation or to adding the BZB fraction to a solvent, allowing BZB to crystallize by cooling and submitting the resulting mixture to solid-liquid separation. In the course of crystallizing the BZB fraction by cooling, adding a solvent in a small amount or setting the crystallization temperature at a slightly higher level helps to form crystals of higher purity or facilitate filtration. Dispersive crystallization in solvent is preferably effected by adding the BZB fraction or the crystals thereof formed by cooling to a solvent to form a dispersion of the crystals. In either case, any solvent may be used satisfactorily as long as it dissolves the impurities present in the BZB fraction and it is not always necessary for the solvent in question to have an ability to dissolve BZB. As the impurities and BZB behave similarly in solvent solubility, however, a solvent capable of dissolving BZB is used. Preferable solvents here are the same as the aforementioned solvents for recrystallization. Whenever the purity falls short of the target level or there occurs a need to remove the adhered solvent after completion of the aforementioned purification by crystallization, an after-treatment is performed in the same as in the case of recrystallization to be described below.

Recrystallization is effected by dissolving the BZB fraction or the crystals obtained therefrom in a solvent and cooling the resulting solution to a temperature below the melting point of BZB, preferably to below 10° C., to separate the crystals. Cooling to below 5° C. is preferable for an efficient recovery of BZB. However, cooling to below −30° C. is not desirable as this will occasionally cause components other than BZB to separate. Use of 5 parts by weight or less of the solvent per 1 part by weight of the BZB fraction is adequate. An excess of the solvent relative to the BZB fraction is undesirable because the recovery of BZB during recrystallization decreases. It is to be noted that the BZB fraction is liquid not only at the time when it distills out but also usually at normal temperature and the fraction as liquid is occasionally dissolved in a solvent. In this invention, dissolving the BZB fraction and crystallizing it in this manner is also referred to as recrystallization. Recrystallization is preferably effected with stirring and the separated crystals of BZB are collected by a procedure for solid-liquid separation such as centrifugal filtration and vacuum filtration.

Since the mother liquor containing the impurities adheres to the crystals, it is necessary to wash the crystals with the same solvent as used in the recrystallization step to obtain high-purity BZB. The crystals can be washed either by adding a washing solvent directly to the surface of the collected crystals or by throwing the crystals in a solvent and filtering them again. In either case, washing of 1 part by weight of the crystals requires 0.5 part by weight or more of the washing solvent. Washing with less than 0.5 part by weight of the solvent cannot remove the impurities in the mother liquor sufficiently and the purity of BZB deteriorates. On the other hand, washing with too much solvent decreases the recovery of BZB, which is not economical.

The solvent-washed crystals are melted by heating to above 18° C., which is the melting point of BZB, and the adhered solvent is distilled off under reduced pressure. In this manner, it is possible to recover economically colorless transparent BZB with a purity of 99.5% or more, useful as raw material for perfumes and pharmaceuticals and applicable to other industrial uses.

PREFERRED EMBODIMENT OF THE INVENTION

EXAMPLE 1

In a 2000 ml stainless steel autoclave fitted with a stirrer and a reflux condenser were placed 1600 g of toluene and 4 g of cobalt acetate and the reaction was carried out at 155° C. and 0.5 MPa for 5 hours by blowing air into the mixture at a rate of 140 Nm$^3$/hr. The unreacted toluene and the main product benzoic acid were removed by distillation from the reaction mixture to give 260 g of the residue (composed of 15.2% benzoic acid, 37.3% BZB, 2.1% fluorenone and 45.4% heavy components). The percent in the examples designates % by weight unless otherwise indicated.

The residue (100 g) was placed in the bottom of a glass distillation column which is 10 mm in inside diameter, filled with metal packings equivalent to 5 theoretical plates, and it was distilled at 2.6 KPa while keeping the reflux ratio at 10 to give 30 g of a BZB fraction boiling at 190–210° C. The BZB fraction was composed of 85.1% BZB, 8.3% benzoic acid, 5.0% fluorenone and 1.6% others.

In a 30 ml round-bottomed flask fitted with a stirrer was placed 10.0 g of the BZB fraction which was liquid at normal temperature, the fraction was cooled to 0° C. with stirring, 5.9 g of the separated crystals was filtered under reduced pressure and washed with 5.9 g of cold isopropanol chilled at 0° C. The crystals were placed in a 30 ml flask and stripped of the solvent by distillation under reduced pressure on a water bath at 60° C. to give 5.1 g of purified BZB. Table 1 shows the recovery of BZB, the purity of BZB and the hue of BZB after purification by crystallization.

COMPARATIVE EXAMPLE 1

The residue (100 g) obtained in Example 1 was placed in the bottom of a glass distillation column which is 10 mm in inside diameter, filled with metal packings equivalent to 5 theoretical plates, and it was distilled at 2.6 KPa while keeping the reflux ratio at 10 to give 35 g of a BZB fraction boiling at 185–200° C. The BZB fraction was composed of 73.0% BZB, 14.6% benzoic acid, 10.9% fluorenone and 1.5% others.

In a 30 ml round-bottomed flask fitted with a stirrer was placed 10.0 g of the BZB fraction, the fraction was cooled to 0° C. with stirring, and 4.0 g of the separated crystals was filtered under reduced pressure and washed with 4.0 g of cold isopropanol chilled at 0° C. The crystals were placed in a 30 ml flask and stripped of the solvent by distillation under reduced pressure on a water bath at 60° C. to give 3.5 g of purified BZB. Table 1 shows the recovery of BZB, the purity of BZB and the hue of BZB after purification by crystallization.

TABLE 1

|  | Recovery of BZB % | Purity of BZB wt % | Hue of BZB Hazen No. |
|---|---|---|---|
| Example 1 | 60.0 | 99.74 | 20 |
| Comparative example 1 | 41.1 | 98.90 | 50 |

EXAMPLE 2

The residue (200 g) obtained by a procedure similar to that in Example 1 was placed in the bottom of a glass distillation column which is 10 mm in inside diameter, filled with metal packings equivalent to 5 theoretical plates, and it was distilled at 2.6 KPa while keeping the reflux ratio at 10 to give 50 g of a BZB fraction boiling at 195–200° C. The BZB fraction was composed of 92.0% BZB, 4.0% benzoic acid, 3.2% fluorenone and 0.8% others.

In a 30 ml round-bottomed flask fitted with a stirrer was placed 10.0 g of the BZB fraction, 10.0 g of isopropanol was added, the fraction was dissolved at 25° C., the resulting solution was cooled to 0° C. with stirring, and 6.2 g of the separated crystals was filtered under reduced pressure and washed with 6.9 g of cold isopropanol chilled at 0° C. The crystals were placed in a 30 ml flask and stripped of the solvent by distillation under reduced pressure on a water bath at 60° C. to give 6.0 g of purified BZB. Table 2 shows the recovery of BZB, the purity of purified BZB and the hue of purified BZB in the course of purification by crystallization.

EXAMPLE 3

In a 30 ml round-bottomed flask fitted with a stirrer was placed 10.0 g of the BZB fraction obtained in Example 2, a mixture of 5.0 g of water and 5.0 g of isopropanol was added, the resulting mixture was cooled from room temperature to 0° C. with stirring, and 7.6 g of the separated crystals was filtered under reduced pressure and washed with a mixture chilled at 0° C. of 3.8 g of water and 3.8 g of isopropanol. The crystals were placed in a 30 ml flask and stripped of the solvent by distillation under reduced pressure on a water bath at 60° C. to give 6.8 g of purified BZB. Table 2 shows the recovery of BZB, the purity of purified BZB and the hue of purified BZB in the course of purification by crystallization.

EXAMPLE 4

In a 30 ml round-bottomed flask fitted with a stirrer was placed 10.0 g of the BZB fraction obtained in Example 2, a mixture of 5.0 g of water and 5.0 g of isopropanol was added, the resulting mixture was cooled from room temperature to 0° C. with stirring, and 7.6 g of the separated crystals was filtered under reduced pressure and washed with a mixture chilled at 0° C. of 7.6 g of water and 7.6 g of isopropanol. The crystals were placed in a 30 ml flask and stripped of the solvent by distillation under reduced pressure on a water bath at 60° C. to give 6.1 g of purified BZB. Table 2 shows the recovery of BZB, the purity of purified BZB and the hue of purified BZB in the course of purification by crystallization.

EXAMPLE 5

In a 30 ml round-bottomed flask fitted with a stirrer was placed 10.0 g of the BZB fraction obtained in Example 2, a mixture of 5.0 g of water and 5.0 g of isopropanol was added, the resulting mixture was cooled from room temperature to 0° C. with stirring, and 7.5 g of the separated crystals was filtered under reduced pressure and washed with a mixture chilled at 0° C. of 7.5 g of water and 7.5 g of isopropanol. The crystals were placed in a 30 ml flask and stripped of the solvent by distillation under reduced pressure on a water bath at 60° C. to give 5.8 g of purified BZB. Table 2 shows the recovery of BZB, the purity of purified BZB and the hue of purified BZB in the course of purification by crystallization.

EXAMPLE 6

In a 30 ml round-bottomed flask fitted with a stirrer was placed 10.0 g of the BZB fraction obtained in Example 2 at room temperature, the fraction was cooled to 15° C. with stirring, and 4.1 g of the separated crystals was filtered under reduced pressure and washed with 3.1 g of cold isopropanol chilled at 0° C. The crystals were placed in a 30 ml flask and stripped of the solvent by distillation under reduced pressure on a water bath at 60° C. to give 3.6 g of purified BZB.

Table 2 shows the recovery of BZB, the purity of purified BZB and the hue of purified BZB in the course of purification by crystallization.

TABLE 2

|  | Recovery of BZB % | Purity of BZB wt % | Hue of BZB Hazen No. |
| --- | --- | --- | --- |
| Example 2 | 65.2 | 99.83 | 10 |
| Example 3 | 73.9 | 99.80 | 20 |
| Example 4 | 66.3 | 99.86 | 5 |
| Example 5 | 63.0 | 99.87 | 5 |
| Example 6 | 39.1 | 99.85 | 10 |

What is claimed is:

1. A process for recovering benzyl benzoate, which comprises:
    oxidizing a reaction mixture of toluene with molecular oxygen in the presence of a metal catalyst;
    removing unreacted toluene and benzoic acid from the reaction mixture to produce a residue;
    distilling said residue remaining after removal of unreacted toluene and benzoic acid from the reaction mixture, thereby separating a fraction of benzyl benzoate containing at least 80 wt% benzyl benzoate, at most 10 wt % benzoic acid and at least 10 wt% fluorenone;
    purifying the fraction of benzyl benzoate by crystallization wherein the purification is effected by recrystallizing said benzyl benzoate in a solvent for recrystallization while controlling a cooling temperature in the range of 10° C. to −30° C. during recrystallization; and
    recovering benzyl benzoate of at least 99.5% purity.

2. The process for recovering benzyl benzoate as described in claim 1, wherein the solvent for recrystallization comprises an aliphatic alcohol with 1 to 5 carbon atoms.

3. The process of claim 1, wherein the solvent comprises at least one aliphatic alcohol selected from the group consisting of methanol, ethanol, propanol, butanol and pentanol.

4. The process of claim 2, wherein the aliphatic alcohol is mixed with water.

5. The process of claim 4, wherein the aliphatic alcohol to water ratio is in the range of approximately 1:2 to 2:1.

6. The process of claim 1, wherein the metal catalyst is cobalt acetate.

7. The process of claim 1, wherein air is used as a source of the molecular oxygen.

8. The process of claim 1, wherein the oxidizing is performed at a temperature of 120–170° C.

9. The process of claim 1, wherein the oxidizing is performed at a pressure of normal up to 1 Mpa.

10. The process of claim 1, wherein the oxidizing is either continuous or batch.

11. The process of claim 1, wherein the reaction mixture contains byproducts that can be at least one selected from the group consisting of water, formic acid, acetic acid, propionic acid, acetone, benzene, biphenyl, methylbiphenyl, dimethylbiphenyl, fluorene, fluorenone, toluic acid, phthalic acid, isophthalic acid, terephthalic acid, biphenylcarboxylic acid, methylbiphenylcarboxylic acid, biphenyldicarboxylic acid, phenylbenzyl alcohol, benzaldehyde, benzyl alcohol, benzyl benzoate, benzyl acetate, benzyl toluate and benzyl biphenylcarboxylate.

12. The process of claim 1, wherein the benzyl benzoate has a hue of no more than 20 Hazen.

13. The process of claim 1, wherein the distilling is performed at a temperature below 270° C.

14. The process of claim 1, wherein the distilling is performed at a pressure of at most 4.0 KPa.

15. The process of claim 1, wherein the distilling is performed using at least 5 theoretical plates.

16. A process for recovering benzyl benzoate, which comprises:
    oxidizing a reaction mixture of toluene with molecular oxygen in the presence of a metal catalyst;
    removing unreacted toluene and benzoic acid from the reaction mixture to produce a residue;
    distilling said residue remaining after removal of unreacted toluene and benzoic acid from the reaction mixture, thereby separating a fraction of benzyl benzoate containing at least 80 wt % benzyl benzoate, at most 10 wt % benzoic acid and at most 10 wt% fluorenone;
    purifying the fraction of benzyl benzoate by crystallization, wherein the purifying of the fraction of benzyl benzoate by crystallization is effected by recrystallizing in a solvent for recrystallization comprising an aliphatic alcohol with 1 to 5 carbon atoms, the recrystallizing being performed at a cooling temperature in the range of 10° C. to −30° C.; and
    recovering high purity benzyl benzoate.

* * * * *